(12) United States Patent
Spencer

(10) Patent No.: US 11,324,279 B2
(45) Date of Patent: May 10, 2022

(54) SHOE INSERT SYSTEM FOR INDUCING POSITIVE FOREFOOT STRIKING

(71) Applicant: Spence Spencer, Phoenix, AZ (US)

(72) Inventor: Spence Spencer, Phoenix, AZ (US)

( * ) Notice: Subject to any disclaimer, the term of this patent is extended or adjusted under 35 U.S.C. 154(b) by 0 days.

(21) Appl. No.: 16/967,247

(22) PCT Filed: Oct. 11, 2019

(86) PCT No.: PCT/US2019/056007
§ 371 (c)(1),
(2) Date: Aug. 4, 2020

(87) PCT Pub. No.: WO2020/077314
PCT Pub. Date: Apr. 16, 2020

(65) Prior Publication Data
US 2021/0037912 A1   Feb. 11, 2021

Related U.S. Application Data

(60) Provisional application No. 62/766,354, filed on Oct. 12, 2018.

(51) Int. Cl.
*A43B 7/28* (2006.01)
*A43B 17/02* (2006.01)
*A61F 5/14* (2006.01)

(52) U.S. Cl.
CPC ............... *A43B 7/28* (2013.01); *A43B 17/02* (2013.01); *A61F 5/14* (2013.01)

(58) Field of Classification Search
CPC .................................. A43B 7/38; A43B 17/02
USPC ............................................................ 36/43
See application file for complete search history.

(56) References Cited

U.S. PATENT DOCUMENTS

| 1,960,418 | A | * | 5/1934 | Schaller | A43B 7/1425 36/178 |
| 5,154,682 | A | * | 10/1992 | Kellerman | A43B 1/0072 36/44 |
| 5,799,414 | A | * | 9/1998 | Kellerman | A43B 1/0072 36/160 |
| 6,000,147 | A | * | 12/1999 | Kellerman | A43B 7/142 36/160 |
| 2009/0025254 | A1 | | 1/2009 | Smith | |
| 2009/0049712 | A1 | * | 2/2009 | Steszyn | A43B 7/1425 36/91 |

(Continued)

*Primary Examiner* — Alissa L Hoey
*Assistant Examiner* — Catherine M Ferreira
(74) *Attorney, Agent, or Firm* — Invention To Patent Services; Alex Hobson

(57) ABSTRACT

A corrective shoe insole system is configured to produce and promote a positive forefoot. A corrective shoe insole system includes an insole having a forefoot portion and a heel portion. The forefoot portion is be thicker than the heel portion to promote forefoot striking when walking or running. An insole may have one or more forefoot risers coupled thereto to provide a specific positive forefoot insole for the user. A user may gradually increase the thickness of live forefoot portion of the insole by adding or changing out forefoot risers. This gradual increase in forefoot thickness of the insole may prevent injury and muscle strain from the adjusted foot striking position. A forefoot riser may be detachably attachable to the forefoot portion of the insole and an attachment feature may provide positive and secure attachment to prevent movement of the forefoot riser.

13 Claims, 4 Drawing Sheets

(56) References Cited

U.S. PATENT DOCUMENTS

2010/0058540 A1  3/2010  Calvert
2012/0117818 A1  5/2012  Slowik
2013/0133223 A1  5/2013  Zake

* cited by examiner

SHOE INSERT SYSTEM FOR INDUCING POSITIVE FOREFOOT STRIKING

CROSS REFERENCE TO RELATED APPLICATIONS

This application is a national stage application of PCT/US2019/0056007, filed on Oct. 11, 2019, which claims the benefit of priority to U.S. provisional patent application 62/766,354, filed on Oct. 12, 2018; the entirety of which is hereby incorporated by reference herein.

BACKGROUND OF THE INVENTION

Field of the Invention

The invention relates to a corrective insole system for inducing positive forefoot striking utilizing an insole that is thicker on a forefoot portion than on a heel portion.

Background

Most of the current shoes on the market are designed to promote a heel strike during walking and especially during running. This action creates a disruption in the central nervous system and inversely effects the motor programs associated with correct movement. The current shoes on the market designed with a negative heel are not able to address all the various needs for different activity or style. Positive refers here to be above, and negative to be below, the level foot resting on floor. Positive forefoot thus tilts the forefoot up. Negative heel tilts the heel downward. The alleged best runners of the world, the African Maasai Tribe people, run with positive forefoot, thus rarely suffer hip-nerve reflex pain.

People participating in recreational activities using positive heel footwear may have reduced performance joint pain and injuries. They may also suffer from leg cramping shin splints, plantar fasciitis, bunions (Hallux Valgus) and related inflammation as a result of improper biomechanics associated with a positive heal shoe.

SUMMARY OF THE INVENTION

The invention is directed to a corrective shoe insole system configured to produce a positive forefoot. An exemplary corrective shoe insole system comprises an insole having a forefoot portion and a heel portion. The forefoot portion is thicker than the heel portion to promote forefoot striking when walking or running. An exemplary insole may have one or more forefoot risers coupled thereto to provide a specific positive forefoot insole for the user. A user may gradually increase the thickness of the forefoot portion of the insole by adding or changing out forefoot risers. This gradual increase in forefoot thickness of the insole may prevent injury and muscle strain from the adjusted foot striking position.

An exemplary insole has a length from a toe end to a heel end. The heel portion of the insole extends from the heel end toward the toe end and may extend into a mid-foot region, or no more than about 70% of the length of the insole. A forefoot portion or forefoot riser extends from the toe end toward the heel end and is configured to extend under the phalanges and metatarsal bones of the foot and may extend into a mid-foot region or no more than about 65% or about 50% of the length of the insole. In some cases, the forefoot portion or a forefoot riser is no more than 35% of the length of the insole.

An exemplary insole has a heel pad and a forefoot pad. The forefoot portion of the insole may be thicker than the heel portion and may be substantially thicker, such as at least 25% thicker and preferably at least 50% thicker than the heel portion, as measured in the center of each portion or under the calcaneus bone for the heel portion. The thickness of a forefoot portion may be about 3 mm thick or more, about 4 mm thick or more, about 6 mm thick or more, about 8 mm thick or more, about 10 mm thick or more, about 12 mm thick or more and any range between and including the thickness values provided, such as from about 3 mm to about 12 mm thick Forefoot risers may be detachably attached to the forefoot portion of the insole to increase the thickness of the forefoot portion incrementally. A forefoot riser may extend over at least a portion of the forefoot portion of the insole, such as from the toe end down toward the heel end. A forefoot riser may only extend about 65% of the length of the insole or less, about 50% of the length of the insole or less, about 35% of the length of the insole or less and any range between and including the length values provided. An exemplary corrective shoe insole system may utilize one or more, two or more, three or more, four or more forefoot risers to incrementally increase the thickness of the forefoot portion of the insole. The forefoot risers may be different thicknesses thereby allowing a user to change out, or substitute a thinner forefoot riser for a thicker forefoot riser as they grow more accustomed to forefoot striking. Alternatively, the forefoot risers may be substantially the same thickness, within about 10%, and a user may simply incrementally add an additional forefoot riser to increase the thickness of the forefoot portion. A forefoot riser may be about 1 mm thick or more, about 2 mm thick or more about 3 mm thick or more, about 4 mm thick or more, about 5 mm thick or more, about 6 mm thick or more and any range between and including the thickness values provided, such as from about 1 mm to about 6 mm thick.

A forefoot riser may be detachably attachable to an insole by coupling an insole attachment feature with a riser attachment feature. Hook-and-loop fastener may be an attachment feature wherein the hook portion of the hook-and-loop fastener is configured on the bottom of the forefoot portion of the insole and the opposing loop portion of the hook-and-loop fastener is configured on the top of the forefoot riser, or vice versa. A forefoot riser may be simply pressed onto the bottom of the forefoot portion of the insole to detachably attach the forefoot riser thereto. Additional forefoot risers may be added using hook-and-loop fastener. A forefoot riser may have hook-and-loop fastener on both the top and bottom to allow two or more forefoot risers to be stacked under the forefoot portion of the insole.

Another exemplary attachment is a protrusion/aperture attachment, wherein the insole has an aperture or recess extending into the bottom of the insole for receiving a protrusion extending from the top of a forefoot riser. This may positively locate the forefoot riser with respect to the insole. Additional forefoot risers may be stacked wherein a second forefoot riser is coupled to a first forefoot riser using a protrusion/aperture attachment. An exemplary forefoot riser may have an aperture extending into the bottom surface for receiving a protrusion extending from the top surface of a second forefoot riser. A forefoot riser may be detachably attached to the insole or to another forefoot riser using the hook-and-loop fastener and/or the protrusion/aperture attachment.

An exemplary protrusion/aperture attachment may be a keyway type attachment, wherein a first component of the insole system, such as the insole, has a keyway shaped aperture and a second component, such as a forefoot riser, has a corresponding keyway shaped protrusion; such as dovetail shaped apertures and protrusion. Note that a protrusion/aperture attachment may be used to couple a first forefoot riser to a second forefoot riser. The bottom of the insole may comprise a plurality of keyway apertures, again such as dovetail shaped, and they may extend across the width to one or both side surfaces of the insole for sliding the keyway shape riser protrusion therein. The keyway shaped apertures may also extend from a toe end of the insole or toe end of a forefoot riser down along the length direction.

An exemplary protrusion/aperture attachment may comprise a keyway shaped aperture having an insert portion and a seat portion. An insert portion may extend to the surface of the insole or forefoot riser and the seat portion may extend from the extended end of the insert portion and may extend transversely from the extended end of the insert portion. A keyway shaped protrusion may include a shank portion and a lock portion. The lock portion may extend up through the insert portion of the aperture and then, upon twisting or rotating, the lock portion may rotate to be retained in the seat portion of the aperture.

An exemplary insole may comprise a pad or padding material that is resilient, wherein the pad returns substantially to an original thickness after removal of a compressive load. An exemplary pad may be an elastomer, such as silicone, urethane, rubber and the like, or a foam, such as a closed cell foam comprising, Ethylene-Vinyl Acetate (EVA), polyurethane (PU), polyethylene (PE) and the like.

An exemplary method of correcting foot striking from heel to forefoot includes an incremental adjustment of the positive forefoot insole. As described herein, a user may initially insert the insole into their shoes and the insole may have a positive forefoot, wherein the forefoot portion is thicker than the heel portion. The difference in thickness of the initial insole may be small and as the user becomes comfortable with this positive forefoot insole, they may then increase the thickness of the insole by detachably attaching a forefoot riser. The additional forefoot riser may increase the forefoot thickness and the user may select a forefoot riser that is comfortable for them. As they grow accustom to this first additional forefoot riser, they may then switch the forefoot riser out for a thicker one, or they may simply add another forefoot riser to the first one to increase the thickness of the forefoot portion of the insole.

An exemplary insole may comprise a toe riser which may be for any one or more of the toes. In particular, a toe riser may be configured for raising the big toe and may be configured on the inside side of the insole. A toe riser extends up from the insole toward the toe end of the insole to produce an angled toe riser support.

An exemplary insole may comprise a toe restraint for retaining one or more of the toes. In particular, a toe restraint may be configured for restraining the big toe to prevent Hallux rigidus, or bunions. An exemplary toe restraint is a loop of material that is attached to the insole. A person simply inserts a toe through the loop and the toe is restrained to the insole in a desired position by the toe restraint.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
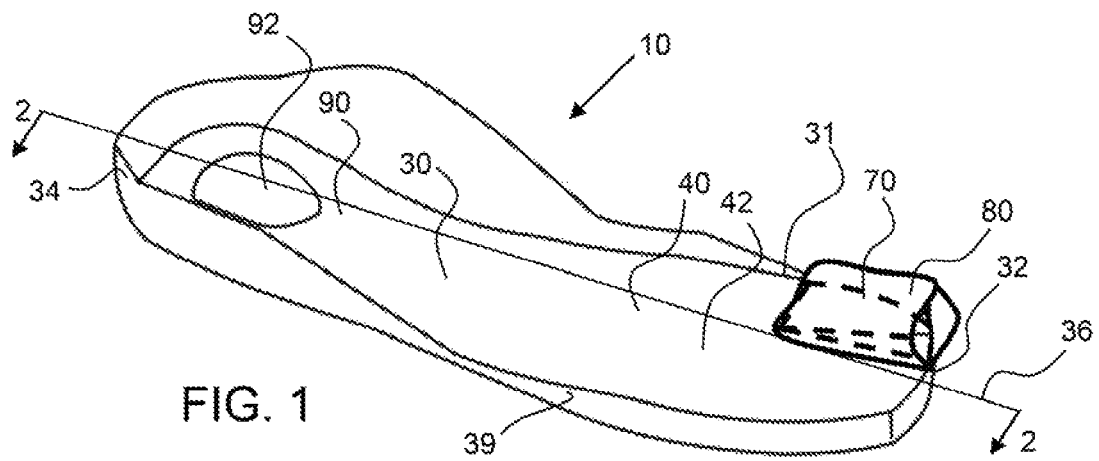
FIG. 1 shows a perspective view of an exemplary corrective shoe insole system comprising an insole having a heel portion and a forefoot portion.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
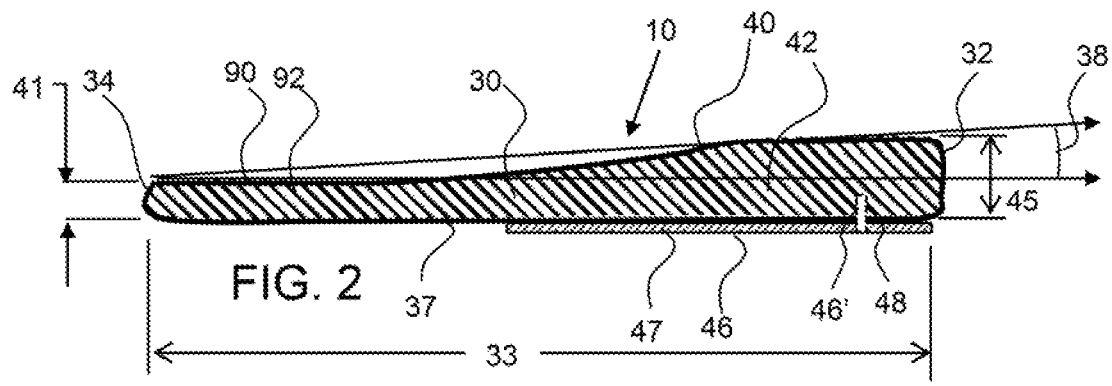
FIG. 2 shows a cross-sectional view of the insole shown in FIG. 1 along line 2-2, wherein the forefoot portion is thicker than the heel portion creating an incline angle.
Figure 3:
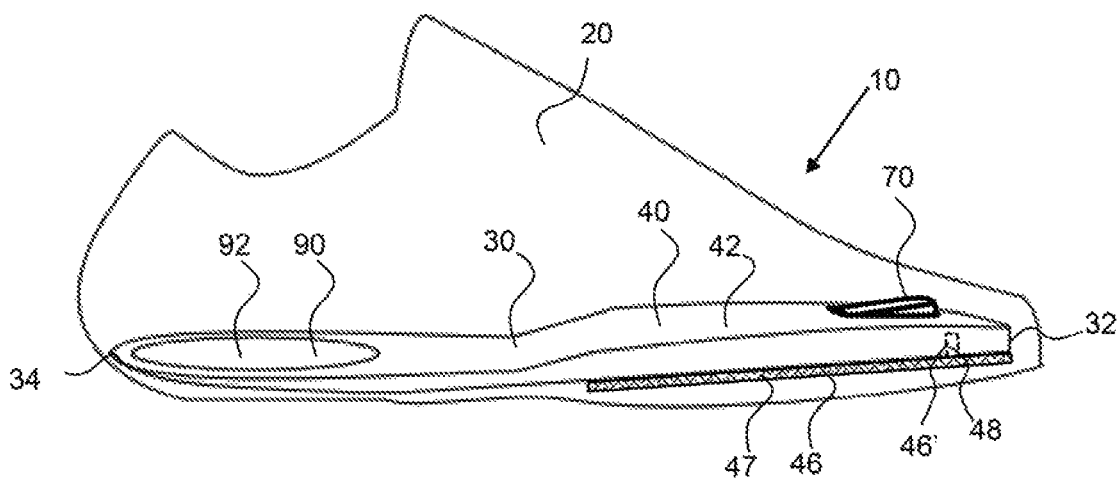
FIG. 3 shows a side view of a shoe having an exemplary insole therein.

Referring now to FIGS. 1 to 3, an exemplary corrective shoe insole system 10 comprises an insole 30 having a heel portion 90 and a forefoot portion 40. The heel portion has a heel pad 92, that may be detachable from the insole and the forefoot portion has a forefoot pad 42. The heel portion may be thinner than the forefoot portion, thereby creating a corrective incline angle 38 that is inclined from horizontal, or from the bottom 37 of the insole. The forefoot portion has a thickness 45 that is substantially thicker, such as at least about 20% thicker and preferably at least 50% thicker, than a heel portion having a thickness 41. Both the heel portion and the forefoot portion may be uniform in thickness over a portion of the length of the respective portion, as shown in FIG. 2. The exemplary insole has a length 33 from a heel end 34 to a toe end 32 that extends along a length axis 36. The length of the insole may be configured to fit any shoe size.

The exemplary insole 30 has a toe restrain 80 for retaining the big toe to prevent or to treat Hallux rigidus as described herein. Also, a toe riser 70, as shown most clearly in FIG. 3 raises the big toe up from the top 35 of the insole 30, to improve balance. Both the toe restraint and toe riser are configured on an inside side 31 of the insole, or on the side configured to receive the big toe. The outside side 39 is the opposing side of the insole and corresponds with the outside of a foot configured thereon.

As shown in FIGS. 2 and 3, an insole attachment feature 46 comprises two separate types of attachments, insole hook-and-loop fastener 47 and an insole aperture 48. The insole hook-and-loop fastener 47 is configured for detachably attaching a forefoot riser having a complimentary hook-and-loop fastener on a top surface. The insole aperture 48 is configured for receiving a riser protrusion extending from the top of a forefoot riser, not shown. One or both of these two types of attachment features may be used for detachably attaching a forefoot riser.

A shown in FIG. 3, the corrective shoe insole system 10 is configured in a shoe 20 and the forefoot portion is thicker than the heel portion to promote positive forefoot striking.

Figure 4:
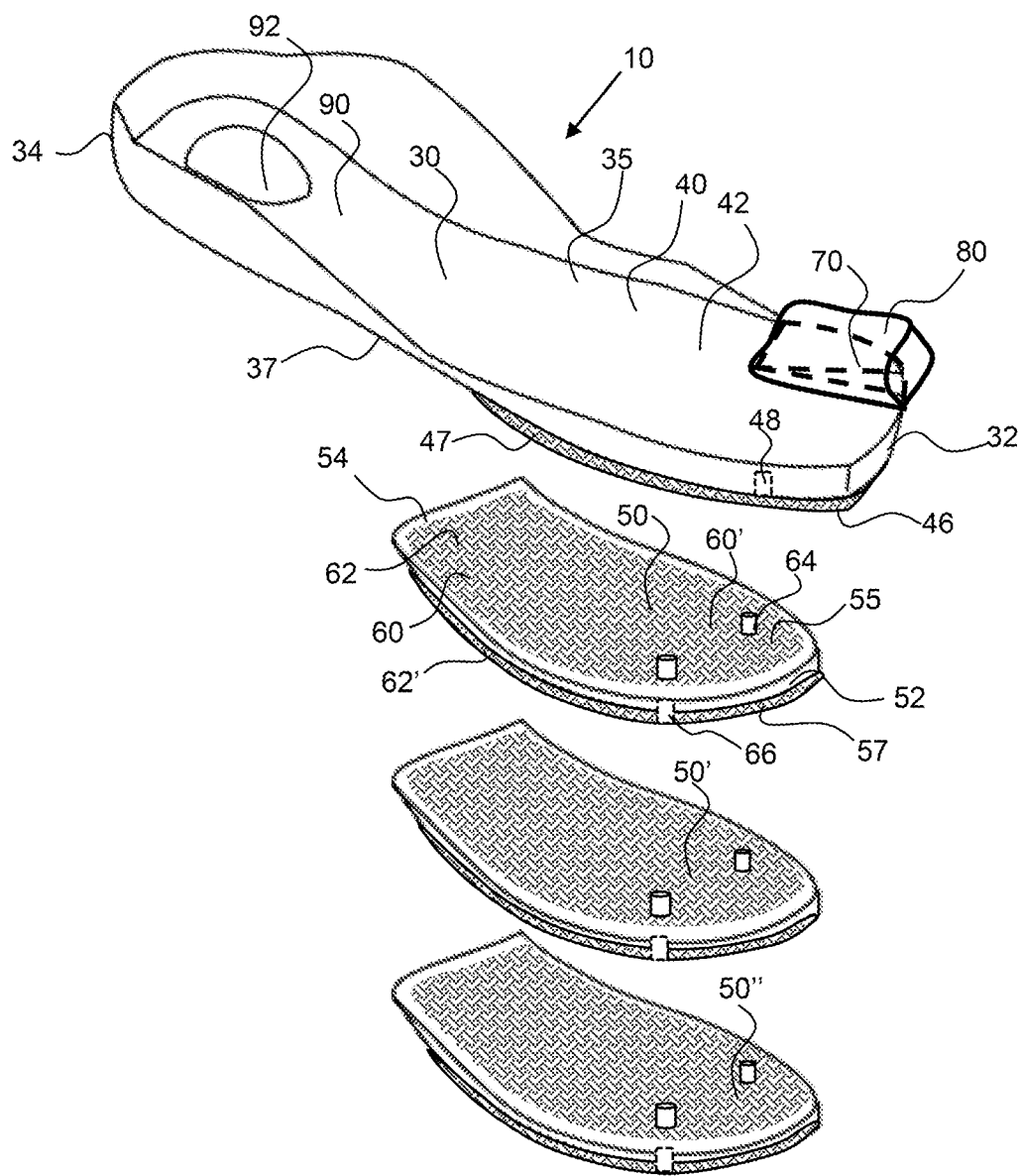
FIG. 4 shows a perspective view of a corrective shoe insole system comprising an insole and a plurality of forefoot risers that are detachably attachable to the insole.

As shown in FIG. 4, an exemplary corrective shoe insole system 10 comprises an insole 30 and a plurality of forefoot risers 50-50" that are detachably attachable to the insole. Each of the forefoot risers has a length from a heel end 54 to a toe end 52 and has a riser attachment feature 60 such as a riser hook-and-loop fastener configured on the top surface 55 for detachably attaching to the insole hook-and-loop fastener 47 configured on the bottom 37 of the insole or to the bottom of another forefoot riser, as shown. A forefoot riser may have a riser hook-and-loop fastener 62' on the bottom 57 of the forefoot riser for attachment of additional forefoot risers to increase the incline angle and overall forefoot thickness. Also, each forefoot riser 50 may comprise a riser protrusion 64, such as a post for extending into an insole aperture 48 or forefoot riser aperture 66. Note that all three of the forefoot risers shown may be coupled to the insole, with forefoot riser 50 coupled directly to the insole 30 and forefoot riser 50' coupled to forefoot riser 50 and finally with forefoot riser 50" coupled to forefoot riser 50'. The insole shown in FIG. 4 has a toe riser 70 and a toe restraint 80 to restrain the big toe.

Figure 5:
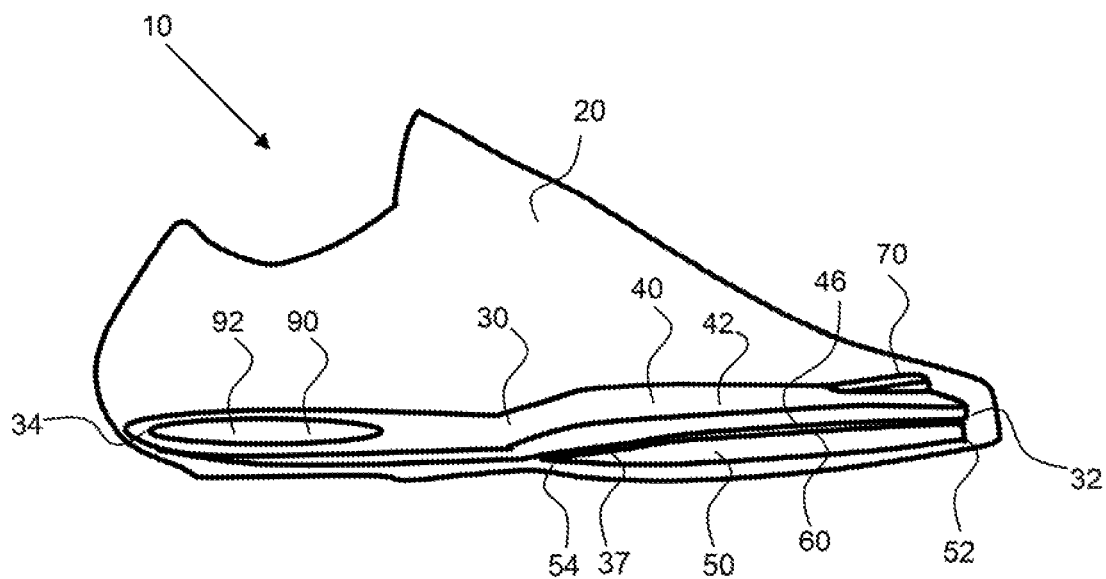
FIG. 5 shows a side view of a shoe having an exemplary insole and one forefoot riser therein.

As shown in FIG. 5, an exemplary corrective insole system 10 includes an insole 30 with a forefoot riser 50 coupled to the bottom 37 of the insole. The insole attachment feature 46 and forefoot riser attachment feature 60 enable detachable attachment of the forefoot riser. Successive forefoot risers may be attached to incrementally increase the thickness of the forefoot insole and cause the person to strike with the forefoot.

Figure 6:
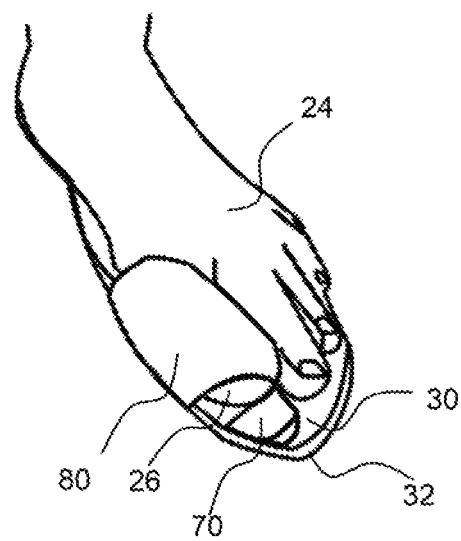
FIG. 6 shows a top view of a person's foot configured on an exemplary insole with their big toe configured in a toe restraint and configured over a toe riser.

As shown in FIG. 6, a person's foot 24 is configured on an exemplary insole 30 with their big toe 26 configured in a toe restraint 80 and configured over a toe riser 70.

Figure 7:
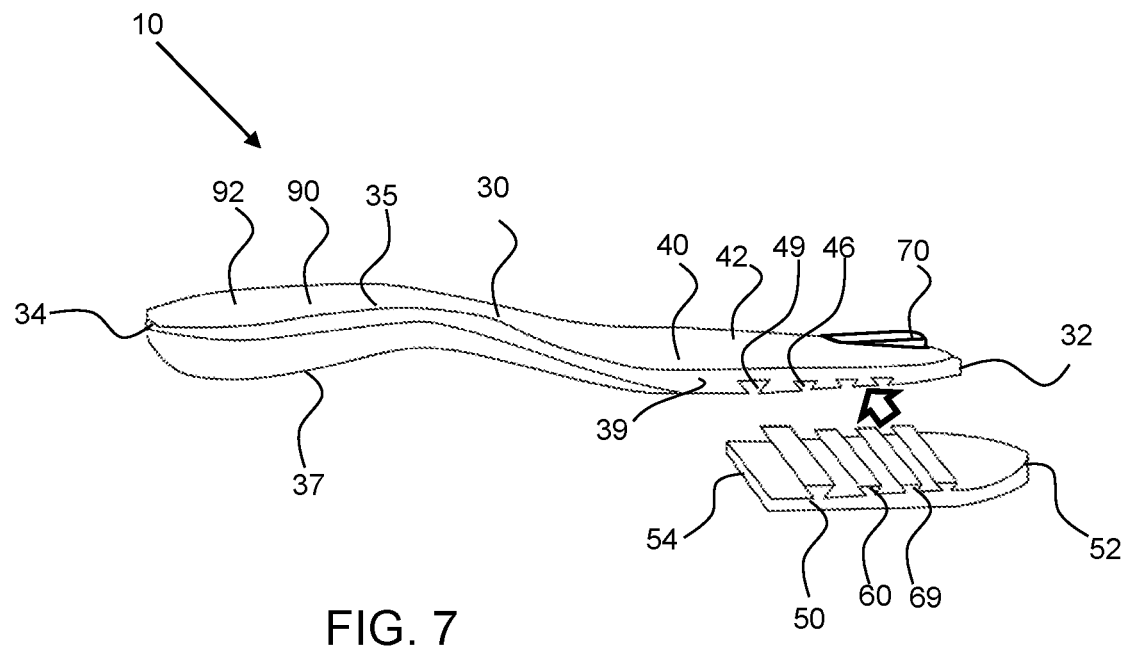
FIG. 7 shows a side view of an exemplary corrective shoe insole system comprising an insole having a heel portion, a forefoot portion and a forefoot riser configured to detachably attach to the bottom of the forefoot portion of the insole.

As shown in FIG. 7, an exemplary corrective shoe insole system 10 comprises an insole 30 having a heel portion 90, a forefoot portion 40 and a forefoot riser 60 configured to detachably attach to the bottom of the forefoot portion of the insole. A dove-tail type insert attachment feature 46 comprises a plurality of keyway shaped apertures 49 for receiving the plurality of keyway shaped riser protrusions 69 extending from the top of the forefoot riser. The keyway shaped apertures 49 extend to the outside side 39 of the insole and extend across the width of the insole. The forefoot riser may be moved into position under the forefoot portion of the insole by aligning the keyway protrusion with the keyway aperture and sliding under the forefoot riser, as indicated by the bold arrow. This type of attachment feature may provide for more positive and secure retaining of the forefoot riser to the insole. A keyway shaped protrusion is larger in dimension on an extended end than an attached end or end attached to the forefoot riser. A keyway shaped aperture is larger in dimension at an extended end, or position offset from the aperture opening, than the at the aperture opening.

Figure 8:
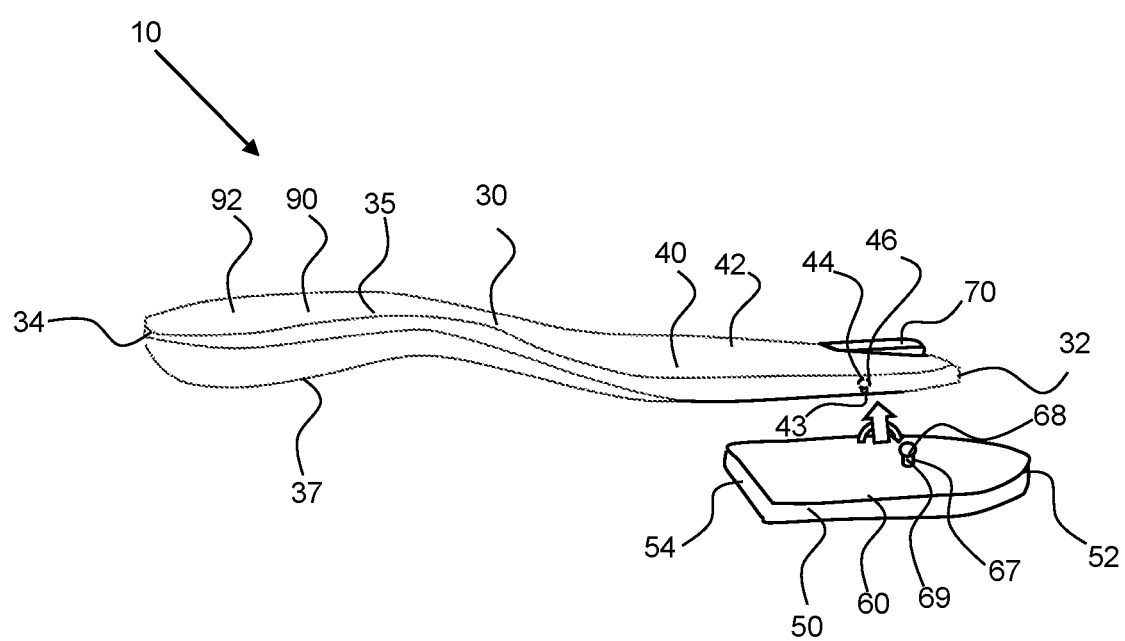
FIG. 8 shows a side view of an exemplary corrective shoe insole system comprising an insole having a heel portion, a forefoot portion and a forefoot riser configured to detachably attach to the bottom of the forefoot portion of the insole.

As shown in FIG. 8, an exemplary corrective shoe insole system 10 comprises an insole 30 having a heel portion 90, a forefoot portion 40 and a forefoot riser 60 configured to detachably attach to the bottom of the forefoot portion of the insole. An insert attachment feature 46 comprises a keyway shaped aperture 49 for receiving the keyway shaped riser protrusion 69 extending from the top of the forefoot riser. The keyway shaped riser protrusion 69 has a narrow shank portion 67 extending from the top of the forefoot riser and a lock portion 68 that is larger in dimension than the shank portion. The keyway shaped aperture 49 has an insert portion 43 for receiving the lock portion and then an angular offset seat portion 44 that enables forefoot riser to be twisted to rotate the lock portion within the seat portion. The keyway shaped riser protrusion 69 may be inserted into the keyway shaped aperture of the insole attachment feature 46 and then rotated, or twisted to lock the keyway shaped riser protrusion into the keyway shaped aperture. This arrangement may prevent the forefoot riser from becoming detached or from moving with respect to the insole. Also, a forefoot riser may have a number of protrusions having the keyway shape, such as having the shank and lock portions. In an exemplary embodiment, two keyway shaped riser protrusions extend from the forefoot riser and are configured to be inserted into separate apertures and then twisted into separate seat portions of the insole keyway shaped aperture.

As shown in FIGS. 7 and 8, the forefoot of the insole 30 is not thicker than the heel portion 90 and the addition of the forefoot riser 60 makes the forefoot portion thicker. This arrangement may allow for minimal increases in forefoot thickness as an initial insole for a user.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present inven-

What is claimed is:

1. A method of correcting foot striking comprising:
   a) providing a shoe insole system comprising:
      an insole comprising:
         a forefoot portion comprising a forefoot pad having a forefoot pad thickness;
         a heel portion comprising a heel pad having a heel pad thickness;
      wherein the forefoot pad thickness is substantially thicker than the heel pad thickness,
      wherein the forefoot pad thickness is at least 50% thicker than the heel pad;
      wherein the insole further comprises an insole attachment feature configured in the forefoot portion;
      wherein the insole attachment feature comprises an insole aperture;
         a first forefoot riser configured to be coupled to the forefoot portion of the insole;
      wherein the first forefoot riser comprises a riser attachment feature comprising a riser protrusion;
      wherein the first forefoot riser is detachably attachable to the insole by said insole attachment feature coupling with the riser attachment feature;
      wherein the first forefoot riser is detachably attachable to the forefoot portion by inserting the riser protrusion into the insole aperture;
         a second forefoot riser having a riser protrusion and wherein the first forefoot riser comprises a riser aperture configured on a bottom of the first forefoot riser that is configured to receive the riser protrusion of the second forefoot riser;
   b) inserting the insole into a shoe;
   c) ambulating in said shoe;
   d) removing the insole and attaching said first forefoot riser to the forefoot portion of the insole to produce a first increased thickness insole having an increased thickness of the forefoot portion of the insole;
   e) inserting the first increased thickness insole into said shoe; and
   f) ambulating with a forefoot strike;
   g) attaching said second forefoot riser to the first forefoot riser to produce a second increased thickness insole;
   h) inserting the second increased thickness insole into said shoe; and
   i) ambulating with a forefoot strike;
   wherein iteratively increasing forefoot riser thickness is configured to prevent injury.

2. The method of claim 1, wherein the first forefoot riser comprises two two riser apertures in said bottom, and wherein the second forefoot riser comprises two riser protrusions, and wherein attaching the second forefoot riser to the first forefoot riser to produce a second increased thickness insole includes inserting the two riser protrusions of the second forefoot riser into the two riser apertures of the first forefoot riser.

3. The method of claim 1, wherein the riser attachment feature of the first forefoot riser comprises two riser protrusions and wherein the insole comprises two insole apertures configured to receive said two riser protrusions.

4. The method of claim 1, wherein the forefoot shoe insole system further comprises a toe riser extending from a top of the insole and located on an inside side of the forefoot portion of the insole and configured to raise the big toe up from said top of the insole.

5. A method of correcting foot striking comprising:
   a) providing a shoe insole system comprising:
      an insole comprising:
         a forefoot portion comprising a forefoot pad having a forefoot pad thickness;
         a heel portion comprising a heel pad having a heel pad thickness;
      wherein the forefoot pad thickness is substantially thicker than the heel pad thickness, wherein the forefoot pad thickness is at least 50% thicker than the heel pad;
      wherein the insole further comprises an insole attachment feature configured in the forefoot portion;
      wherein the insole attachment feature comprises an insole aperture;
         a first forefoot riser configured to be coupled to the forefoot portion of the insole;
      wherein the first forefoot riser comprises a riser attachment feature comprising a riser protrusion; and
      wherein the first forefoot riser is detachably attachable to the insole by said insole attachment feature coupling with the riser attachment feature;
         wherein the first forefoot riser is detachably attachable to the forefoot portion by pressing the riser protrusion into the insole aperture;
         a second forefoot riser having a sweater thickness than the first forefoot riser;
      wherein the second forefoot riser is configured to be coupled to the forefoot portion of the insole;
      wherein the second forefoot riser comprises a riser attachment feature comprising a riser protrusion; and
      wherein the second forefoot riser is detachably attachable to the insole by said insole attachment feature coupling with the riser attachment feature; and
         wherein the second forefoot riser is detachably attachable to the forefoot portion by pressing the riser protrusion into the insole aperture;
   b) inserting the insole into a shoe;
   c) ambulating in said shoe;
   d) removing the insole and attaching said first forefoot riser to the forefoot portion of the insole to produce a first increased thickness insole having an increased thickness of the forefoot portion of the insole;
   e) inserting the first increased thickness insole into said shoe; and
   f) ambulating with a forefoot strike;
   q) removing the first forefoot riser from the first increased thickness insole;
   h) attaching said second forefoot riser having a greater thickness than the first forefoot riser to produce a second increased thickness insole;
   i) inserting the second increased thickness insole into said shoe; and
   i) ambulating with a forefoot strike; and
   wherein iteratively increasing forefoot riser thickness is configured to prevent injury;
      wherein the forefoot shoe insole system further comprises a Hallux toe restraint extending over the toe riser and configured to restrain the big toe down on the toe riser, wherein the Hallux toe restraint is configured to prevent Hallux rigidus or bunions.

6. The method of claim 1, wherein the forefoot shoe insole system further comprises a Hallux toe restraint extending from a top of the insole and located on an inside side of the forefoot portion of the insole and configured to restrain the big toe, wherein the Hallux toe restraint is configured to prevent Hallux rigidus or bunions.

7. The method of claim 1, wherein the insole aperture is a keyway shaped aperture;
   wherein the riser attachment feature comprises a keyway shaped riser protrusion comprising a shank portion extending from a top of the forefoot riser and a lock portion that is larger in dimension than the shank portion; and
      the forefoot riser is detachably attachable to the forefoot pad by sliding the keyway shaped protrusion into the keyway shaped aperture.

8. The method of claim 7,
   wherein the second forefoot riser comprises a keyway shaped riser protrusion configured for insertion into the keyway shaped aperture of the insole.

9. The method of claim 7, wherein the forefoot shoe insole system further comprises a toe riser extending from a top of the insole and located on an inside side of the forefoot portion of the insole and configured to raise the big toe up from said top of the insole.

10. The method of claim 9, wherein the forefoot shoe insole system further comprises a Hallux toe restraint extending over the toe riser and configured to restrain the big toe down on the toe riser, wherein the Hallux toe restraint is configured to prevent Hallux rigidus or bunions.

11. The method of claim 7, wherein the forefoot shoe insole system further comprises a Hallux toe restraint extending from a top of the insole and located on an inside side of the forefoot portion of the insole and configured to restrain the big toe, wherein the Hallux toe restraint is configured to prevent Hallux rigidus or bunions.

12. The method of claim 1, wherein the first forefoot riser is configured to extend under the phalanges and metatarsal bones of a foot when said insole, with said first forefoot riser attached, is inserted into said shoe and when said foot is inserted into said shoe.

13. The method of claim 12, wherein the first forefoot riser and second forefoot riser extend no more than 65% of a length of the insole from a toe end of said insole.

* * * * *